(12) United States Patent
Boyes et al.

(10) Patent No.: US 6,617,494 B2
(45) Date of Patent: Sep. 9, 2003

(54) METHODS FOR IDENTIFYING TRANSGENIC PLANTS USING MORPHOLOGICAL MARKERS

(75) Inventors: Douglas C. Boyes, Chapel Hill, NC (US); Carol M Hamilton, Apex, NC (US); Andreas Kloti, Durham, NC (US); Jorn Gorlach, Durham, NC (US); Neil Hoffman, Chapel Hill, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/832,589

(22) Filed: Apr. 11, 2001

(65) Prior Publication Data

US 2002/0004939 A1 Jan. 10, 2002

Related U.S. Application Data

(60) Provisional application No. 60/196,753, filed on Apr. 12, 2000.

(51) Int. Cl.[7] .......................... C12N 15/87; C12N 15/89
(52) U.S. Cl. ...................... 800/278; 800/287; 435/468; 435/469; 435/470
(58) Field of Search .................... 800/290, 270, 800/293, 298, 294, 278; 435/419, 468, 470; 536/23.1

(56) References Cited

FOREIGN PATENT DOCUMENTS

| WO | 9741228 | 11/1997 |
|---|---|---|
| WO | 98 59062 | 12/1998 |

OTHER PUBLICATIONS

Schwechheimer et al (2000, Funct Intergr Genomics 1:35–43).*
Songstad et al (1995, Plant Cell, Tissue and Organ Culture 40:1–15).*
Oppenheimer et al (1991, Cell 67:483–493, listed in IDS).*
Schnittger, A. et al.; "Generation of a Spacing Pattern: The role of TRIPTYCHON in Trichome Patterning in *Arabidopsis*"; The Plant Cell. Jun. 1999; vol. 11(6): pp. 1105–1116.
Oppenheimer, David.G.; "T myb Gene Required for Leaf Trichome Differentiation in *Arabidopsis* is Expressed in Stipules"; Cell. Nov. 1991; vol. 67: pp. 483–493.
Herman, Patricia. L. et al.; "Trichome Development in *Arabidopisis thaliana* II. Isolation and Complementation of the GLABROUS1 Gene"; The Plant Cell. Nov. 1989; vol. 1(11): pp. 1051–1055.
Ingram, G.C. et al.; "Parallels between Unusual Floral Organs and Fimbriata, Genes Controlling Flower Development in *Arabidopsis* and *Antirrhinum*"; The Plant Cell. Sep. 1995 vol. 7(9): pp. 1501–1510.
Szymanski, D B. et al.; "A regulator of *Arabidopsis* Trichome Initiation"; Genetics. Jun. 1998; vol. 149(2):pp. 565–577.
Guyer et al. (1998) "Activation of latent transgenes in *Arabidopsis* using a hybrid transcription factor" *Genetics* 149:633–639.
Wilde et al. (1994) "Control of gene expression in plant cells using a 434:VP16 chimeric protein" *Plant Molec. Biol.* 24:381–388.
Aoyama and Chua (1997) "A glucocorticoid–mediated transcriptional induction system in transgenic plants" *The Plant Journal* 11:605–612.
Schwechheimer et al. (1998) "The activities of acidic and glutamine rich transcriptional activation domains in plant cells: design of modular transcription factors for high–level expression" *Plant Molec. Biol.* 36:195–204.
Moore et al. (1998) "A transcription activation system for regulated gene expression in transgenic plants" *PNAS* 95:376–381.
Molina et al. (1999) "Inhibition of protoporphyrinogen oxidase expression in *Arabidopsis* causes at a lesion–memic phenotype that induces systemic acquired resistance" *The Plant Journal* 17:667–678.

* cited by examiner

Primary Examiner—Elizabeth F. McElwain
Assistant Examiner—Stuart F. Baum
(74) Attorney, Agent, or Firm—Laura L. Kiefer; Timothy G. Hofmeyer; Deborah H. Spencer (57) ABSTRACT

Morphological markers are used in a method of visually identifying plants transformed with a nucleotide sequence (e.g., a heterologous gene). The nucleotide sequence is transformed into a plant that exhibits an abnormal phenotype for a morphological marker. If the transformation of the plant is successful, the progeny of the transformed plant will exhibit a normal phenotype. In a preferred embodiment, the plant is Arabidopsis and the morphological marker is Gl1, which is associated with trichome production on plant leaves. The method is also useful for identifying plants that are homozygous for the transformed gene, and for identifying transformants in the T2 generation that are true crosses, rather than self-crosses.

21 Claims, 7 Drawing Sheets

Fig. 1. The glabrous1 mutant lacks trichomes.

Arabidopsis thaliana, Columbia Wild type (1X)

Glabrous1 mutant (1X)

(10X view of Glabrous1 mutant)

(10X view of Columbia Wild type) — trichome

Fig. 2. *glabrous1* plants transformed with the *GL1* gene contain trichomes

Fig. 3

Fig. 4. Segregation of the glabrous1 gene in T2 progeny from selfed T1 plants

Fig. 5. Segregation of GL1 in the F1 progeny of a cross between a T1 target line to a homozygous gl1 driver line

Fig. 6 Use of PPG360 to identify homozygous transgenics

Fig. 7 Use of PPG360 to identify transgenics crossed into the driver line

Target construct is transformed into driverless glabrous line

Glabrous line containing the target construct is crossed with a driver line

METHODS FOR IDENTIFYING TRANSGENIC PLANTS USING MORPHOLOGICAL MARKERS

CROSS-REFERENCE TO RELATED APPLICATIONS

This application claims the benefit of U.S. Provisional Application No. 60/196,753 filed Apr. 12, 2000.

FIELD OF THE INVENTION

This invention relates to methods of identifying transgenic plants and methods of monitoring the segregation of genes in the progeny of transgenic plants.

BACKGROUND OF THE INVENTION

One of the primary goals of plant genetic research and development is the production of transgenic plants that express a heterologous gene (i.e., produce a protein or an RNA from a gene that normally does not occur in the plant) in an amount sufficient to confer a desired phenotype to the plant. While significant advances have been made in pursuit of this goal, the transformation of heterologous genes into certain plants and the expression of these genes in the plants remains problematic.

In general, plant transformation refers to stably introducing a nucleic acid segment carrying a functional gene (generally, a heterologous gene) into a plant that did not previously contain that gene. In a successful transformation, a DNA construct containing a structural coding sequence is inserted into the genome of a plant by one of several known methods. Examples of known transformation methods include direct gene transfer into protoplasts, microprojectile bombardment, injection into protoplasts, cultured cells and tissues or meristematic tissues, electroporation, and Agrobacterium-mediated transformation.

After effecting delivery of heterologous DNA to recipient cells and plants by any of the methods listed above, identifying the cells and plants exhibiting successful or enhanced expression of a heterologous gene for further culturing and plant regeneration generally occurs by one or more screening methods.

"Screening" generally refers to identifying the cells and/or plants exhibiting expression of a heterologous gene that has been transformed into the plant. Usually, screening is carried out to select successfully transformed seeds (i.e., transgenic seeds) for further cultivation and plant generation (i.e., for the production of transgenic plants). In *Arabidopsis thaliana*, generally only about 0.5–1% of the seed produced by the transformed plants will contain the heterologous gene of interest. In order to improve the ability to identify transformants, a selectable or screenable marker gene is normally transformed into plant along with the heterologous gene of interest. In such a case, one would then generally assay the potentially transformed cells, seeds or plants by exposing the cells, seeds, plants, or seedlings to a selective agent or agents. For example, transgenic cells, seeds or plants may be screened under selective conditions, such as by growing the seeds or seedlings on media containing selective agents such as antibiotics (e.g., hygromycin, kanamycin, or paromomycin), the successfully transformed plants having been transformed with genes encoding resistance to such selective agents. Alternatively, other methods (e.g., exposing plants transformed with herbicide-resistant genes to herbicides such as BASTA®) are used to screen the cells, seeds, plants or tissues of the plants for the desired marker gene.

To additionally confirm the presence of the heterologous nucleic acid or "transgene(s)" in the seeds of the transformed plant or in the regenerated plants produced from those seeds, a variety of assays may be performed. Such assays include, for example, molecular biological assays, such as Southern and Northern blotting and PCR; biochemical assays, such as detecting the presence of a protein product, by immunological means (ELISAs and Western blots) or by enzymatic function; and by plant part assays, such as leaf or root assays.

Despite the many methods currently available for screening plants for successful transformation, these methods are not without certain disadvantages. Often, the inclusion of the selective marker gene in the transforming vector places undesirable stress on the plant. Challenging the plants with one or more selective agents further subjects the plant to additional stresses that may be detrimental to the future growth of the plant. For the analysis of unstressed plants, it would necessary to identify transgenic plants using a non-selective marker. Green fluorescent protein (GFP) has been used to screen transformants (see European Patent Application EP 19970924602 assigned to Pioneer Hi-Bred International, Inc.). However, methods of using non-selective markers are presently not widely used, and the development of additional methods of utilizing non-selective markers to screen transformants is desirable.

Methods of detecting successfully transformed plants utilizing nonselective markers would also find use in preliminary screening of primary transformants. In general, primary transformants are not analyzed, because the transformation process can result in multiple insertions (i.e., undesirable mutations). Generally, it is desirable to either out-cross or self-cross the primary transformants to allow the mutations and/or transgenes to segregate. It would be useful to identify primary transformants by selection and then screen for the transformants to be analyzed in the segregating progeny under non-selective conditions.

Furthermore, in smaller plants such as those of the Arabidopsis species (i.e., *Arabidopsis thaliana*), it is often necessary to bulk seed in order to obtain sufficient material for an analysis of successful transformation. It would be desirable to have a method of identifying transformants in such smaller plants without being required to use methods such as seed bulking in order to obtain sufficient material to analyze transformants.

Finally, it would be useful for breeding purposes to be able to determine, in the $F_2$ population, whether or not a particular plant is homozygous for a particular gene or not. Presently, it is not possible to make such a determination without extensive genetic analyses of the plant.

In view of the foregoing, there is clearly a need for a method of determining whether or not a plant has been successfully transformed without using selective markers, and without having to resort to invasive or destructive assay techniques.

SUMMARY OF THE INVENTION

The present inventors have discovered a new method for efficiently, quickly and reliably determining by visual detection whether a particular plant has been successfully transformed with a heterologous gene.

One aspect of the invention is a method for determining the successful transformation of a plant with a heterologous gene. The method is carried out by transforming a first plant with a target DNA construct comprising at least one heterologous gene operatively associated with a morphological marker that encodes a normal phenotypical characteristic of the plant, wherein the plant is homozygous for a mutation of the morphological marker that renders the plant abnormal for the phenotypical characteristic. Seeds are then collected from the first plant and at least one progeny plant grown therefrom. The phenotype of the progeny plant is then detected, wherein the presence of the normal phenotype as indicated by the characteristic encoded by the morphological marker indicates the successful transformation of the progeny plant with the heterologous gene.

An additional aspect of the invention is a method of detecting the successful transformation of a Arabidopsis plant with a heterologous gene. This method of the invention is carried out by transforming a first Arabidopsis plant that is homozygous for a mutation of the GL1 gene with a target DNA construct comprising a heterologous gene operatively associated with the wild-type GL1 gene. The plant is allowed to produce seeds, which are grown into progeny Arabidopsis plants. The presence or absence of trichomes on the progeny Arabidopsis plant is then detected, wherein the presence of trichomes indicates the successful transformation of the progeny plant with the heterologous gene.

Plants that are homozygous for a mutation of a morphological marker that renders the plant abnormal for the phenotypical characteristic further comprising a target DNA construct with at least one heterologous gene operatively associated with a morphological marker that encodes a normal phenotypical characteristic of the plant are also an aspect of the present invention. In a preferred embodiment, the plant is Arabidopsis, and the plant is homozygous for a gl1 mutation.

In addition to providing a method of visually determining whether a particular plant has been successfully transformed with a heterologous gene, the present invention allows the practitioner to track the transgenic state of a plant through successive generations, and track the segregation of transgenes throughout subsequent generations of plant progeny. The methods of the present invention also advantageously allow for the visual determination of the homozygosity, or lack thereof of a transformed plant. The present invention also advantageously allows the practitioner to distinguish between true crosses and self-crosses in plants that have been cross-fertilized.

The foregoing and other aspects of the present invention are explained in detail in the specification set forth below.

BRIEF DESCRIPTION OF THE DRAWINGS

A photographic comparison of wild type (*Arabidopis thaliana*, Columbia wild type) and glabrous (*Arabidopis thaliana*, glabrous 1 mutant) leaves are presented in FIG. 1, with 1× magnification (top photographs) and 10× magnification (bottom photographs) shown to reveal the presence of trichomes on the wild type plant. The glabrous mutant is homozygous for a mutation in the gl1 gene.

FIG. 3 is a map of the transformation vector PPG358. The plasmid contains a minimal promoter (4XUAS gal4 minimal promoter) followed by multiple cloning sites for cloning in transgenes, followed by the OCS terminator. Downstream is the Arabidopsis glabrous 1 (GL1)gene expressed from its own promoter. Downstream from Gl1 is the BAR gene encoding resistance to the herbicide BASTA™, expressed from the NOS promoter. In the case of the vector PPG359, the GL1 promoter is replaced by the 35S promoter. In the case of the transformation vector PPG360, the Gl1 promoter is replaced by the minimal promoter.

FIG. 6 is a schematic illustration of the use of construct PPG360 (see description of FIG. 3) to identify plants homozygous for a heterologous gene (i.e., a transgene). PPG360 contains a heterologous gene and the wild type Gl1 expressed from a minimal promoter. A plant comprising a driver line carrying a mutated gl1 gene and a mutated cot1 gene does not have trichomes. This plant is transformed using an Agrobacterium binary vector carrying the wild type Gl1 gene, the BAR gene and an additional heterologous gene. The result of this transformation yields progeny (T1 generation) of three kinds: (1) a super-high expressing hemizygote with trichomes on both the leaves and cotyledons of the plants; (2) a non-expressing hemizygote with no trichomes; and (3) a high-expressing hemizygote with trichomes on the leaves only. The high-expressing hemizygote of the T1 generation is self-crossed and then screened for the presence or absence of trichomes. It is predicted that such a self-cross will yield in the T2 generation one non-transgenic plant (no trichomes), two hemizygotes (trichomes on the leaves only), and one homozygote (trichomes on both leaves and cotyledons).

FIG. 7 is a schematic illustration of the use of the PPG360 to identify transgenics crossed into the driver line. A first plant that is homozygous for a mutation of the Gl1 gene (i.e., a homozygous gl1 background) is transformed using an Agrobacterium vector carrying the wild type GL1 gene downstream from a minimal promoter, the BAR gene and a heterologous gene. One result of this transformation is a non-expressing hemizygote progeny selected for resistance to the herbicide BASTA™. Crossing a male plant of the non-expressing hemizygote progeny with a female plant comprising the driver line (i.e., no GL1 gene, no heterologous gene) will yield plants that have no trichomes (and thus can be definitively stated to be not transformed) and plants that have trichomes (i.e., progeny that are true crosses representing transformants in the driver line, rather than self-crosses).

DETAILED DESCRIPTION OF THE PREFERRED EMBODIMENTS

Certain advantages and novel features of the invention will be set forth in the description that follows, and will become apparent to those skilled in the art upon examination of the following, or may be learned with the practice of the invention.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

A. Morphological Markers

The present invention utilizes morphological markers and mutations thereof in methods of determining whether or not a plant has been successfully transformed. Morphological markers may be defined herein as nucleic acid sequences (i.e., genes) with known locations in an organism's genome which encode or are correlated with visible structures of the organism (i.e., the plant). In a preferred embodiment, the visible structure of the plant correlated with a morphological marker is a trichome. Trichomes are specialized hair cells that are found on the epidermal surfaces (i.e., on the surfaces of the leaves, stems, petioles, sepals, etc.) of almost all terrestrial plants. In Arabidopsis, trichomes are composed of large single cells, often with multiple branches, that develop early during the differentiation of the plant epidermis. See D. B. Szymanski et al., Genetics 149, 565–577 (1998) and D. G. Oppenheimer et al., Cell 67, 483–493 (1991).

Morphological markers useful in the present invention are those which, when normally expressed (i.e, in the wild type form) cause the plant to have a visually observable phenotypical characteristic (e.g., when the morphological marker is normally expressed, the plant has trichomes, or the plant is of a particular size, or the plant has a particular shape of leaf, or the plant forms a crown gall, etc). However, when these morphological markers are mutated, the mutation causes the plant to exhibit visually observable characteristics that differ from the normal phenotype (i.e., the visually observable characteristic encoded or correlated with the morphological marker is abnormal when the morphological marker is mutated). For example, a plant that normally has trichomes does not have trichomes or has fewer trichomes when the morphological marker is mutated; a plant of normal size is dwarfed when the morphological marker is mutated; a plant that has a certain shape of leaf has a different shape of leaf when the morphological marker is mutated, etc.

A "mutation" as used herein, may be an addition, insertion, deletion or substitution of one or more nucleotides in the morphological marker, which may cause the addition, insertion, deletion or substitution,of one or more amino acids in the polypeptide encoded by the nucleic acid sequence of the morphological marker. Mutations in the morphological markers of the present invention may lead to the creation of stop codons resulting in truncated polypeptides; removal of stop codons resulting in extended polypeptides; or a frameshift resulting in a polypeptide lacking the function of the polypeptide encoded by the gene.

Any morphological marker known to the skilled artisan is useful in the practice of the present invention. However, in a preferred embodiment of the invention, the morphological marker is one that affects the production or development of trichomes on a plant. Trichomes are large single-celled epidermal hairs common to most plants. In Arabidopsis plants, trichomes are regularly distributed on leaves, sepals, and stems but are absent from cotyledons. At least 24 genes are known to regulate aspects of trichome initiation and morphogenesis. See, e.g., D. B. Syzmanski, et al., Genetics 149, 565–577 (1998); M. Hulskamp, et al., Cell 76, 555–566 (1994); and M. D. Marks, Annu. Rev. Plant Physiol Plant Mol. Biol. 48, 137–163 (1997).

Mutation of most of these genes (also referred to as "loci") influences cell enlargement and trichome morphology, resulting in abnormal shaped trichomes. Three markers or loci that play a role in the initiation of trichomes are Gl1 (glabra), TTG1 (transparent testa glabra) and Try (triptychon). In Arabidopsis, recessive mutations at two loci, TTG1 and GL1, are known to affect the trichome initiation process in that plants homozygous for mutations at either TTG or Gl1 fail to initiate the trichome development pathway.

The nucleic acid sequence of the wild type Gl1 gene is set forth in D. G. Oppenheimer et al, Cell 67, 483–493 (1991). Mutations of Gl1 are expressed herein as "gl1." All known alleles of gl1 result in a loss of trichomes; however the exact phenotype varies depending on the specific allele. For example, plants homozygous for the gl1-1 allele display a loss of trichomes on leaf surfaces, petioles and sepals. In contrast, plant homozygous for the gl1-43 allele lack only stem trichomes, whereas the trichomes on gl1-2 mutants are reduced in number on leaves and stems but are not completely absent.

While mutations at the Gl1 locus lead to plants with decreased or absent trichomes, mutations at the Try locus affect the spacing of trichomes, which form clumps in try mutant plants. See Huskamp et al., Cell 76, 555–566 (1994). Mutations at another glabra locus, Gl2, have some features in common with TTGl1, although mutants of Gl2 have rudimentary trichomes, suggesting the fate of these cells has already been determined. See Koornneef, Arabid. Inform. Serv. 18, 45–51(1981). Another gene that has been found to be a regulator of Arabidopsis trichome initiation is Cot1. See D. B. Szymanski et al., Genetics 149, 565–577 (1998). Cot1 affects trichome inititation during late stages of leaf development. Id.

Genes whose mutations are associated with abnormal shapes of trichomes include Rhd1, Rhd2, Rhd3 and Rhd4. See J. Schiefelbein, and C. Somerville, Plant Cell, 2, 235–243 (1990). One gene associated with a decreased number of root hairs is Rhd6, whose mutants can be complemented with a plant hormone such as auxin. See J. D. Masucci and J. W. Schiefelbein, Plant Physiol. 106, 1335–1346 (1994). Another gene known as CPC is described in U.S. Pat. No. 5,831,060 to Wada et al. The CPC gene promotes the formation of root hairs in Arabidopsis.

In view of the foregoing, morphological markers useful in the present invention include but are not limited to Gl1, Gl2, Gl3, TTG1, Try, Cot1, CPC, Rhd1, Rhd2, Rhd3, Rhd4 and Rhd6, with Gl1 and Cot1 being preferred. Gl1 is particularly preferred because mutations in the Gl1 locus are highly specific for trichome initiation, so these mutants are generally vigorous, fertile plants. Additionally, trichomes appear on the first true leaves so transformed mutants can be identified at early stages of plant growth.

B. DNA Constructs and Agrobacterium-Mediated Transformation

The present invention is useful in determining whether a plant has been successfully transformed with a heterologous gene. The present invention is also useful in determining whether a plant has been successfully transformed with a homologous gene, as described herein. As used herein, the term "transformation" refers to the stable introduction of a nucleic acid segment (preferably, a DNA construct as described herein) carrying a functional gene (generally, a heterologous gene) into a plant, plant tissue, or plant cell that did not previously contain that gene. In the practice of the present invention, plants to be transformed may be transformed by any transformation means known in the art, including but not limited to direct gene transfer into protoplasts, microprojectile bombardment, injection into protoplasts, cultured cells and tissues or meristematic tissues, electroporation, and Agrobacterium-mediated transformation, with Agrobacterium-mediated transformation being particularly preferred.

The term "heterologous" is used to indicate that a nucleic acid sequence (i.e., a gene) or a protein has a different natural origin with respect to its present host (i.e., a cell or plant that into which it is transformed). "Heterologous" is also used to indicate that one or more of the domains present in a protein differ in their natural origin with respect to other domains present. "Homologous" is used to indicate that a nucleic acid sequence or a protein is of the same natural origin as its present host (i.e., a cell or plant that into which it is transformed). "Expression" refers to the transcription and translation of a structural heterologous nucleic acid to yield the encoded protein. When Agrobacterium-mediated transformation is used in the practice of the invention, the heterologous nucleic acid to be expressed is preferably incorporated into the T-region and is flanked by T-DNA border sequences of the Agrobacterium vector.

Any heterologous gene or nucleic acid that is desired to be expressed in a plant is suitable for the practice of the present invention. Heterologous genes to be transformed and expressed in the plants of the present invention include but are not limited to genes that encode resistance to diseases and insects, genes conferring nutritional value, genes conferring antifungal, antibacterial or antiviral activity, and the like. Alternatively, therapeutic (e.g., for veterinary or medical uses) or immunogenic (e.g., for vaccination) peptides and proteins can be expressed in plants transformed with the according to the present invention. Likewise, the transfer of any nucleic acid for controlling gene expression in a plant is contemplated as an aspect of the present invention. For example, the nucleic acid to be transferred can encode an antisense oligonucleotide. Alternately, plants may be transformed with one or more genes to reproduce enzymatic pathways for chemical synthesis or other industrial processes. Heterologous nucleic acids useful in the present invention may be naturally occurring and may be obtained from prokaryotes or eukaryotes (e.g., bacteria, fungi, yeast, viruses, plants, insects, and mammals), or the nucleic acids may be synthesized in whole or in part.

DNA constructs (also referred to herein as DNA vectors) of the present invention comprise the nucleotide sequence of a morphological marker as described herein, operatively associated with at least one heterologous gene of interest. The preparation of DNA constructs is well known in the art. See, e.g., Sambrook et al., *Molecular Cloning: A Laboratory Manual* (1989). The DNA constructs of the present invention are useful in the transformation of cells (e.g., plant cells), and thus useful in the expression of heterologous genes in the cells. The expression of a heterologous DNA sequence (i.e., gene) in a plant requires proper transcriptional initiation regulatory regions that are recognized in the host plant to be transformed, with the regions linked in a manner which permits the transcription of the coding sequence and subsequent processing in the nucleus. Thus, a DNA construct preferably contains some or all of the necessary elements to permit the transcription and ultimate expression of the coding sequence in the host plant. In addition to the nucleic acid sequences encoding the DNA binding domain and the TATA binding domain, the DNA constructs of the present invention will preferably contain additional regulatory sequences. Examples of such regulatory sequences include but are not limited to promoters, enhancers, signal sequences, polyadenylation sequences, introns, 5' and 3' noncoding regions, terminators, and the like.

DNA constructs comprising the morphological marker sequence and at least one heterologous gene sequence operatively associated therewith are referred to herein as "target" DNA constructs. In a particularly preferred embodiment of the invention, the target DNA construct is introduced into a plant in concert with another DNA construct known as a "driver" DNA construct (e.g., by co-transformation or by sequential transformation of the two constructs). The "driver" construct comprises particular domains such as a DNA-binding domain and a transcriptional activation domain. The DNA binding domain recognizes the regulatory region of the target DNA construct, which recognition leads to the activation of transcription of the genes located on the target DNA construct, as further described herein. When the target DNA and driver DNA constructs are present in the same cell of a plant, the plant is preferably homozygous for a mutation of the morphological marker located on the target DNA construct. In this embodiment of the invention, the plant may be referred to as a "background." For example, if the plant is homozygous for the gl1-1 mutation, the plant may be referred to as a "homozygous gl1-1 background."

In another embodiment of the invention, one plant is homozygous for the driver DNA construct, while another plant is hemizygous for the target DNA construct (i.e., there are two transgenic plants). In this alternative embodiment of the invention, the target DNA construct, and the driver DNA construct are in separate transgenic plants, one of which fertilizes (e.g., pollinates) the other with genetic material (i.e., pollen) to produce reproductive material, such as seed, which may be grown into plants expressing the heterologous gene. The driver line is homozygous for a mutation of the endogenous gene corresponding to the morphological marker. The target line is hemizygous, having received one wild type gene by transformation with the target DNA construct. The plants are sexually crossed in order to activate transcription of the target DNA construct, and the progeny of the plants examined for the presence of the target. The progeny of the cross will all carry the driver construct; the presence of the morphological marker indicates the presence of the target. In this embodiment, the plant homozygous for the driver DNA construct can be referred to as a member of a "driver line."

In yet another embodiment of the invention, a plant that is a member of the driver line as described above is transformed with a target DNA construct, which construct may be located on a vector such as a plasmid, and preferably a vector suitable for Agrobacterium transformation.

Driver DNA constructs of the present invention generally comprise DNA sequences encoding an activation domain. Activation domains may be defined as amino acid sequences that, when combined with the DNA binding domain, increase or activate productive transcription initiation by RNA polymerases. (See generally Ptashne, *Nature* 335, 683–689 (1988)). The activation domain may comprise one or more sequences of amino acids that affect the operation of transcription factors during pre-initiation and assembly at the TATA box of the target DNA construct. The effect of the activation domain is to allow repeated transcription initiation events, leading to greater levels of gene expression. Generally, activation occurs when a transcriptional activation moiety is brought into sufficient proximity to the DNA-binding domain. The DNA-binding domain and the activation domain may be derived from a single transcriptional activator having separate DNA-binding and transcriptional activation domains, found, for example, in the yeast Gal4 and Gcn4 proteins. These functional moieties may also be synthetic.

In recombinant plant expression vectors, the DNA-binding domain and the activation domain may from be derived from different proteins that originate from different organisms. For example, in certain plant expression vectors, the DNA-binding domain is derived from the *E. coli* protein LexA, while the transcriptional activation domain is derived from the transcriptional activator of herpes simplex virus Type I Vp16 protein. When the transcriptional activation domain functions to increase or activate transcription by binding to the regulatory sequences upstream of the gene to be transcribed in trans orientation to the regulatory sequence (as opposed to in cis orientation to the regulatory elements), the activation domain may properly be referred to as a "transactivation domain," and the activation of transcription as "transactivation."

Transactivation domains that may be used in the method of the present invention include but are not limited to VP16 (isolated from the herpes simplex virus), C1 (isolated from maize), and Thm18 (isolated from tomato). Different transactivation domains are known to have different degrees of effectiveness in their ability to increase transcription initiation. One of the most efficient activator domains known is contained in the carboxyl-terminal 100 amino acids of the herpes simplex virus (HSV) virion protein 16 (VP16), also known as Vmw65 or β-gene trans-inducing factor. See Sadowski et a., *Nature* 335, 563–564 (1988); Triezenberg et al., *Genes & Dev.* 2, 718–729 (1988).

Additional flexibility in controlling heterologous gene expression in plants may be obtained by using DNA binding domains and regulatory sequences from heterologous sources (i.e., DNA binding domains from non-plant sources). Some examples of such heterologous DNA binding domains include the LexA and GAL4 DNA binding domains. The LexA DNA-binding domain is part of the repressor protein LexA from *Escherichia coli* (*E. Coli*) (Brent and Ptashne, *Cell* 43:729–736 (1985))

The DNA sequences that comprise the DNA constructs of the present invention are preferably carried on suitable vectors, which are known in the art. Preferred vectors are plasmids that may be propagated in a plant cell. Particularly preferred vectors for transformation are those useful for transformation of plant cells or of Agrobacteria, as described further below. For Agrobacterium-mediated transformation, the preferred vector is a Ti-plasmid derived vector. Other appropriate vectors which can be utilized for carrying the DNA constructs of the present invention are known in the art. For example, suitable vectors for transforming plant tissue and protoplasts have been described by deFramond, A. et al., *Bio/Technology* 1, 263 (1983); An, G. et al., *EMBO J.* 4, 277 (1985); and Rothstein, S. J. et a., *Gene* 53, 153 (1987).

Both the target DNA constructs and the driver DNA constructs of the present invention may contain suitable promoters for the expression of heterologous genes in plants. The term "promoter" refers to the nucleotide sequences at the 5' end of a structural gene which direct the initiation of transcription. Generally, promoter sequences are necessary, but not always sufficient, to drive the expression of a downstream gene. In the construction of heterologous promoter/structural gene combinations, the structural gene is placed under the regulatory control of a promoter such that the expression of the gene is controlled by promoter sequences. The promoter is positioned preferentially upstream to the structural gene and at a distance from the transcription start site that approximates the distance between the promoter and the gene it controls in its natural setting. As is known in the art, some variation in this distance can be tolerated without loss of promoter function. As used herein, the term "operatively linked" or "operatively associated" means that a promoter is connected to a coding region in such a way that the transcription of that coding region is controlled and regulated by that promoter. Means for operatively linking a promoter to a coding region are well known in the art.

As used herein, the term "minimal promoter" is intended to describe a partial promoter sequence which defines the start site of transcription for the linked sequence to be transcribed, but which by itself is not capable of initiating transcription efficiently, if at all. Thus, the activity of such a minimal promoter is dependent upon the binding of a transcriptional activator to an operatively linked regulatory sequence. The term "strong promoter" is defined as a promoter that that has a high affinity for RNA polymerase (generally, a higher affinity than the promoter controlling the gene in its natural state) and that would accordingly be expected to aid in obtaining high gene expression (i.e., generally higher expression than would be obtained when the gene is expressed in its natural state).

In a preferred embodiment of the invention, the driver DNA construct is under the control of a strong promoter, while the target DNA construct is under the control of a minimal and preferably synthetic promoter.

For expression in plants, suitable promoters must be chosen for the host cell, the selection of which promoters is well within the skill of one knowledgeable in the art. Promoters useful in the practice of the present invention include, but are not limited to, constitutive, inducible, temporally regulated, developmentally regulated, chemically regulated, tissue-preferred and tissue-specific promoters.

Numerous promoters are known or are found to facilitate transcription of RNA in plant cells and can be used in the DNA construct of the present invention. Examples of suitable promoters include the nopaline synthase (NOS) and octopine synthase (OCS) promoters, the light-inducible promoter from the small subunit of ribulose bis-phosphate carboxylase promoters, the CaMV 35S and 19S promoters, the full-length transcript promoter from Figwort mosaic virus, histone promoters, tubulin promoters, or the mannopine synthase promoter (MAS). The promoter may also be one that causes preferential expression in a particular tissue, such as leaves, stems, roots, or meristematic tissue, or the promoter may be inducible, such as by light, heat stress, water stress or chemical application or production by the plant. Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters.

Additional promoters useful in the present invention include but are not limited to one of several of the actin genes, which are known to be expressed in most cell types. Yet another constitutive promoter useful in the practice of the present invention is derived from ubiquitin, which is another gene product known to accumulate in many cell types. The ubiquitin promoter has been cloned from several species for use in transgenic plants (e.g., sunflower (Binet et al., *Plant Science* 79: 87–94 (1991); and maize (Christensen et al, *Plant Molec. Biol.* 12, 619–632 (1989)). Further useful promoters are the U2 and U5 snRNA promoters from maize (Brown et al., *Nucleic Acids Res.* 17, 8991 (1989)) and the promoter from alcohol dehydrogenase (Dennis et al., *Nucleic Acids Res.* 12, 3983 (1984)).

Tissue-specific or tissue-preferential promoters useful in the present invention in plants are those which direct expression in root, pith, leaf or pollen. Such promoters are disclosed in U.S. Pat. No. 5,625,136 (herein incorporated by reference in its entirety). Also useful are promoters which confer seed-specific expression, such as those disclosed by Schernthaner et al., *EMBO J.* 7: 1249 (1988); anther-specific promoters ant32 and ant43D; anther (tapetal) specific promoter B6 (Huffman et al., *J. Cell. Biochem.* 17B, Abstract #D209 (1993)); and pistil-specific promoters such as a modified S13 promoter (Dzelkalns et al., *Plant Cell* 5,855 (1993)).

Other plant promoters may be obtained, preferably from plants or plant viruses, and may be utilized so long as the selected promoter is capable of causing sufficient expression in a plant resulting in the production of an effective amount of the desired protein. Preferred constitutive promoters include but are not limited to the CaMV 35S and 19S promoters (see U.S. Pat. No. 5,352,605, the disclosure of which is incorporated herein in its entirety). Any promoter used in the present invention may be modified, if desired, to alter their control characteristics. For example, the CaMV 35S or 19S promoters may be enhanced by the method described in Kay, et al. *Science* (1987) Vol. 236, pp.1299–1302.

As provided above, the preferred method of transformation used in the present invention is Agrobacterium-mediated transformation. A system for Agrobacterium-mediated transformation comprises a vector of at least one strain of *Agrobacterium tumefaciens* or *Agrobacterium rhizogenes*, preferably *Agrobacterium tumefaciens*. In a preferred embodiment of the present invention, the Agrobacterium-mediated transformation comprises an Agrobacterium binary vector.

A variety of Agrobacterium strains are known in the art and may be used in the methods of the invention. See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl Genet. NY* 19, 148 (1993); Ishida et al., *Nature Biotechnol.* 14, 745 (1996); and Komari et al., *The Plant Journal* 10, 165 (1996), the disclosures of which are incorporated herein by reference in their entirety.

Any suitable Agrobacterium vector for transforming a plant may be employed according to the present invention. Agrobacterium is a plant pathogen that transfers a set of genes encoded in a region called T-DNA of the Ti and Ri plasmids of *A. tumefaciens* and *A. rhizogenes*, respectively, into plant cells. In addition to the T-region, the Ti (or Ri) plasmid contains a vir region. The vir region is important for efficient transformation, and appears to be species-specific. Binary vector systems have been developed where the manipulated disarmed TDNA carrying, for example, heterologous DNA and the vir functions are present on separate plasmids. In other words, a heterologous nucleic acid sequence (i.e., gene or genes) of interest and the flanking T-DNA can be carried by a binary vector lacking the vir region. The vir region is then provided on a disarmed Ti-plasmid or on a second binary plasmid. In this manner, a modified T-DNA region comprising heterologous DNA is constructed in a small plasmid which replicates in *E. coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. As another alternative, the heterologous nucleic acid sequence and the T-DNA border sequences can be put into the T-DNA site on the Ti-plasmid through a double recombination event by which the new T-DNA replaces the original Ti-plasmid T-DNA. The vir region can be supplied by the Ti-plasmid or on a binary plasmid. As yet a further alternative, the heterologous nucleic acid sequence and flanking T-DNA can be integrated into the bacterial chromosome as described by U.S. Pat. No. 4,940,838 to Schilperoort et al., and the vir region can then be supplied on a Ti-plasmid or on a binary plasmid. Binary vectors as described herein are useful in the practice of the present invention, and are preferred.

Alternately, in other embodiments of the invention, superbinary or "supervirulent" Agrobacterium vectors are employed in the Agrobacterium solutions. See, e.g., U.S. Pat. No. 5,591,615 and EP 0 604 662, herein incorporated by reference. Such a super-binary vector has been constructed containing a DNA region originating from the hypervirulence region of the Ti plasmid pTiBo542 (Jin et al., *J. Bacteriol.* 169, 4417 (1987)) contained in a supervirulent *A. tumefaciens* A281 exhibiting extremely high transformation efficiency (Hood et al., *Biotechnol* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (see Japanese Patent Appl. (Kokai) No. 4-222527, European Patent Applications EP 504,869 and EP 604,662, and U.S. Pat. No. 5,591,616, herein incorporated by reference) and pTOK233 (see Komari, *Plant Cell Reports* 9,303 (1990), and Ishida et al., *Nature Biotechnology* 14, 745 (1996); herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virc and virG genes from the virulence region of pTiBo542. The plasmid also contains an antibiotic resistance gene, a selectable marker gene, and, if desired, a nucleic acid of interest to be transformed into the plant. Super-binary vectors of the invention can be constructed having the features described above for pTOK162. The T-region of the super-binary vectors and other vectors for use in the invention may be constructed to have restriction sites for the insertion of, for example, heterologous genes to be delivered to the monocot plant. Alternatively, heterologous nucleic acids to be transformed can be inserted in the T-DNA region of the vector by utilizing in vivo homologous recombination. See, Herrera-Esterella et al., *EMBO J.* 2, 987 (1983); Horch et al., *Science*

223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

Although binary vectors and specifically super-binary or supervirulent vectors are preferred in the practice of the present invention, other vectors known in the art (i.e., integrating vectors) may also be used at the discretion of the skilled artisan.

Preferably, Agrobacterium vectors utilized in the methods of the present invention are modified by recombinant nucleic acid techniques to comprise the heterologous nucleic acid (i.e., a gene or genes of interest) to be expressed in the transformed cells, as well as the morphological marker operatively associated therewith. If the target DNA construct is being co-transformed with a driver DNA construct, then a second Agrobacterium vector is modified by recombinant nucleic acid techniques to comprise the elements and domains of the driver DNA construct.

In a preferred embodiment of the invention, recipient cells for transformation are plant cells, more preferably dicot plant cells, even more preferably Arabidopsis species plant cells, and most preferably Arabidopsis thaliana plant cells. As used herein, the term "plants" and the grammatical equivalents thereof include plant cells in plant tissue and plant tissue and plant cells and protoplasts in culture. Plant tissue includes differentiated and undifferentiated tissues of plants, including but not limited to, roots, shoots, leaves, pollen, seeds, tumor tissue and various forms of cells in culture, such as single cells, protoplasts, embryos and callus tissue. The plant tissue may be in plant, or in organ, tissue or cell culture.

After the transformation process is completed, the plant may be subjected to optional resting and/or decontamination steps. In a decontamination step, the plants are contacted with or administered an antibiotic capable of inhibiting the growth of Agrobacterium. Antibiotics known in the art to inhibit Agrobacterium include cefotaxime, timetin, vancomycin, carbenicillin, and the like. Concentrations of the antibiotic will vary according to what is standard for each antibiotic and may be optimized for a particular transformation protocol without undue experimentation by the skilled artisan. The antibiotic may be administered using methods of submersion, spraying, aerosol, and the like. The optional resting step can be performed in the absence of any selective pressures to permit recovery and proliferation of transformed cells. In the resting phase, plants are preferably allowed to rest in the dark or under subdued light, and most preferably in the absence of direct sunlight. The resting and decontamination steps may be carried out either together or in conjunction, in either order; alternatively one step may be carried out but not the other. Each optional step may be carried out for as long as is necessary to inhibit the growth of Agrobacterium (in the case of the decontamination step) or to increase the number of transformed cells (in the case of the resting step). Typically, the resting and decontamination steps (either individually or in conjunction) may be carried out for 1 to 7 days, preferably for 1 to 3 days, and more preferably for 1 to 2 days.

Transgenic plants comprising the DNA constructs of the present invention (as present, for example, in a DNA construct of the present invention, or a transformed cells of the present invention) are also an aspect of the present invention. Procedures for cultivating transformed cells to useful cultivars are known to those skilled in the art. Techniques are known for the in vitro culture of plant tissue, and in a number of cases, for regeneration into whole plants. A further aspect of the invention are plant tissue, plants or seeds containing the DNA constructs described above. Preferred are plant tissues, plants or seeds containing those DNA construct which are mentioned as being preferred.

The invention thus relates, in certain embodiments, to transgenic plants comprising the DNA constructs of the present invention. As used herein, the term "transgenic plants" is intended to refer to plants that have incorporated DNA sequences, including but not limited to genes which are not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

The transformed cells, identified by selection or screening and cultured in an appropriate medium that supports regeneration as provided herein, will then be allowed to mature into plants. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. After the regenerating plants have reached the stage of shoot and root development, they may be transferred to a greenhouse for further growth and testing. Progeny may be recovered from the transformed plants and tested for expression of the exogenous expressible gene by, for example, localized application of an appropriate substrate to plant parts such as leaves, or the "dipping" of such plant parts into solutions comprising the appropriate substrates.

The transformed plants themselves and/or the seeds produced by the plants are then screened to determine if the plants (or certain cells of the plants) have been successfully transformed by the method of the present invention. Advantageously, screening of successful transformants may be carried out by visual inspection of the plant. Since the heterologous gene is transformed with the morphological marker, the restoration of the normal phenotype of the plant for the characteristic encoded or associated with the morphological marker indicates that the plant was successfully transformed. For example, if the morphological marker used is GL1, then plants that exhibit trichomes may be considered successful transformants.

Progeny of the transformed plants may be continuously screened and selected for the continued presence of the integrated heterologous gene in order to develop improved plant and seed lines. The heterologous gene can be moved into other genetic lines by a variety of techniques, including classical breeding, protoplast fusion, nuclear transfer and chromosome transfer.

Any plant that is able to be transformed by DNA may be used in the practice of the present invention, including but not limited to fruit, tobacco, potato, barley, rice, legume, wheat, Brassica or Arabidopsis, with Arabidopsis being preferred. The selection of the plant may be dependent on a number of factors such as the ease of growing the plant and the desired phenotypic trait.

C. Applications of the Present Invention

As set forth above, the present invention is useful in easily screening plants for successful transformation. Plants that are successfully transformed will have normal phenotypes for the morphological marker used by the practitioner and located on the target DNA construct. Accordingly, transformants may be recognized by visual inspection without the requirement of using selective agents or techniques. Of course, the practitioner may still elect to use selective methods as set forth above if, for example, the heterologous gene transformed with the morphological marker is also a selectable marker.

Figure 1:
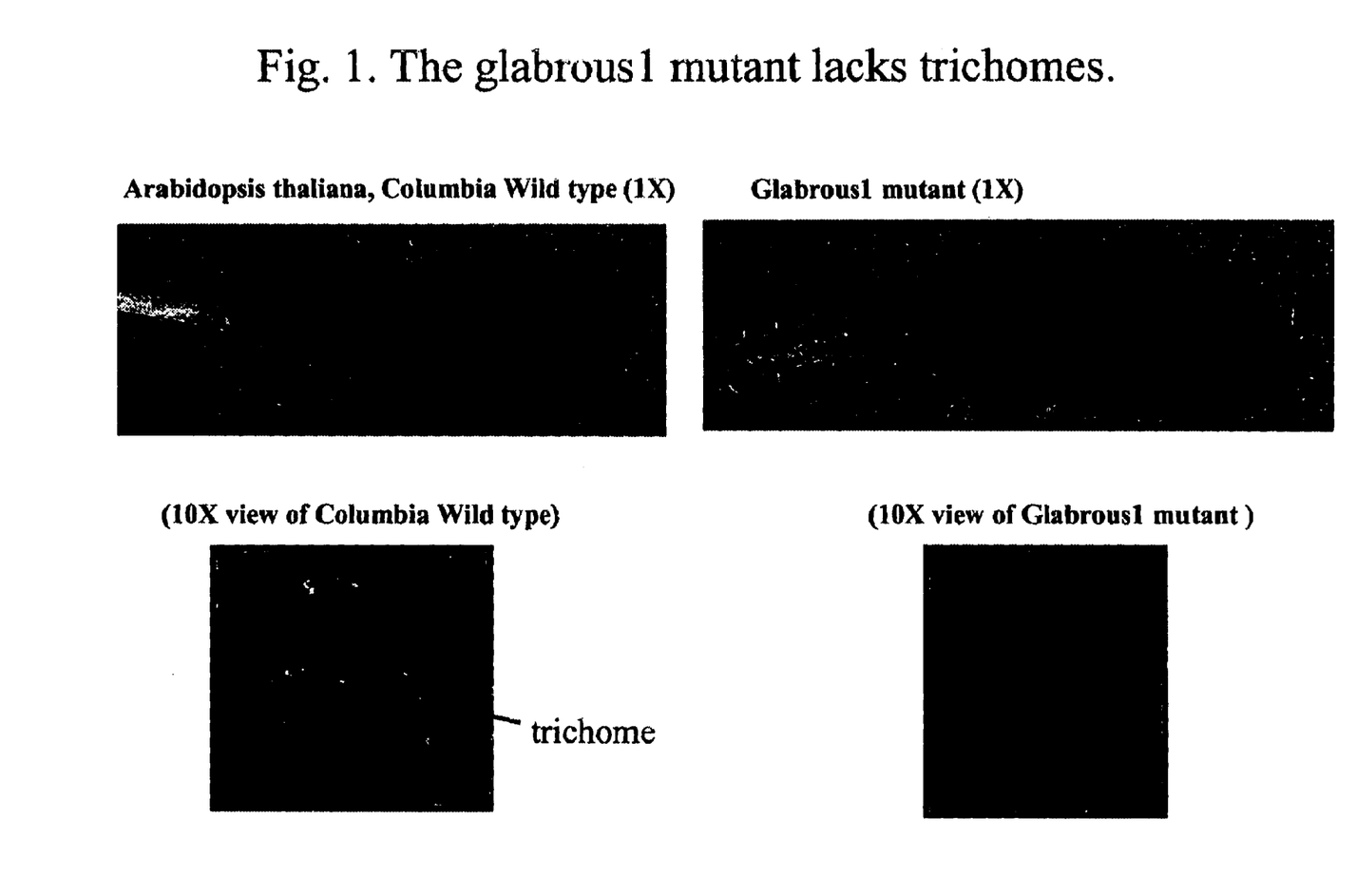
Figure 2:
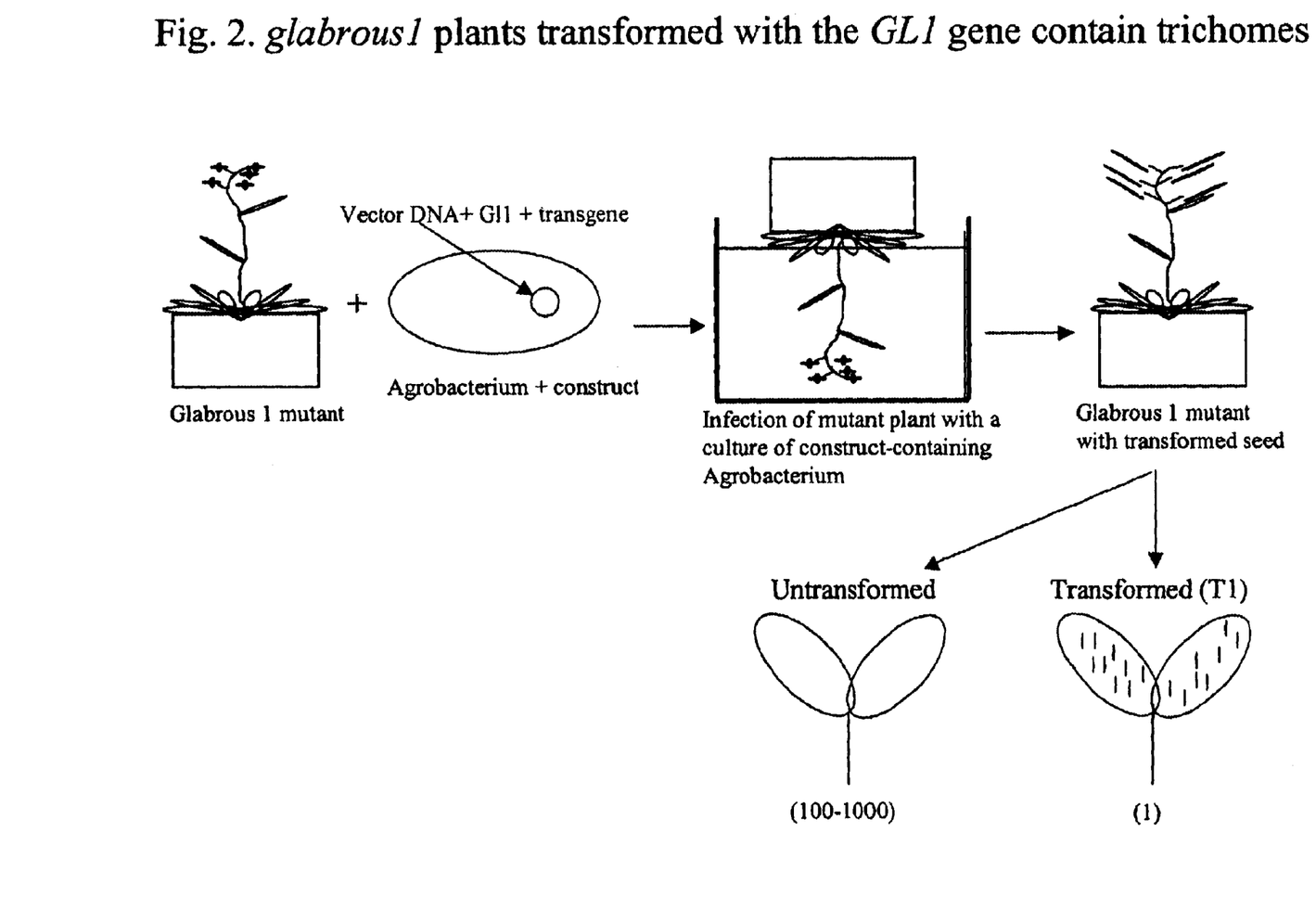
As illustrated in FIG. 2, glabrous plants can be restored to wild type by transformation with the wild type Gl1 gene. If the transforming vector also contains a heterologous gene between the T-DNA borders of an Agrobacterium vector (as shown in FIG. 3), it is likely that the trichome-containing progeny will be transformed with both Gl1 and the heterologous gene.

The method described above is also useful in the identification of primary transformants. The primary transformants of the present invention will be hemizygous, i.e., they will contain one transgenic allele at each locus of insertion. When outcrossed to non-transgenic lines, half the progeny will be hemizygous while the other half will lack the transgene (see FIG. 1). Assuming a single integration site, when the primary transformants are selfed, the transgene will segregate in the T2 population as follows: one fourth of the progeny will lack the transgene, one half will be hemizygous, and one fourth will be homozygous for the transgene.

Additionally, the present invention uses a visually detectable or observable morphological marker to identify transgenic plants in a segregating F1 population, and to identify homozygotes in a segregating F2 population. The marker can also be used to identify transgenics among the primary transformants (T1 population) if a selectable marker will not be employed.

The present invention finds further use in the differentiation of homozygous transgenic plants and hemizygous transgenic plants. Homozygotes are often the more desirable transgenic progeny because they usually express higher levels of the transgene and breed "true." Under currently used methods, it is extremely time consuming and expensive to identify homozygous and high expressing lines. Homozygous lines are commonly identified by observing the segregation of the marker in the T3 generation. To identify high expressing lines, it is common to sample each plant and perform a destructive assay. The present invention circumvents these expensive and time consuming procedures by permitting easy identification of homozygotes (and hence the potentially high expressers) in the early stages of the T2 generation.

This method of detecting homozygotes is aided by the observation that high expression of Gl1, for example, reduces the number of trichomes on the first true leaf. In an additional embodiment of the invention using Gl1 as a first morphological marker, a second site mutation in the Cot1 locus restores the trichome number and results in ectopic expression of trichomes on the plant cotyledons. Cotyledon trichomes only result when the Gl1 is highly expressed in the homozygote, but not in the hemizygote. Accordingly, the practitioner can distinguish hemizygotes from homozygotes based on the presence of trichomes on the cotyledon in the Cot1 mutant background.

Figure 3:
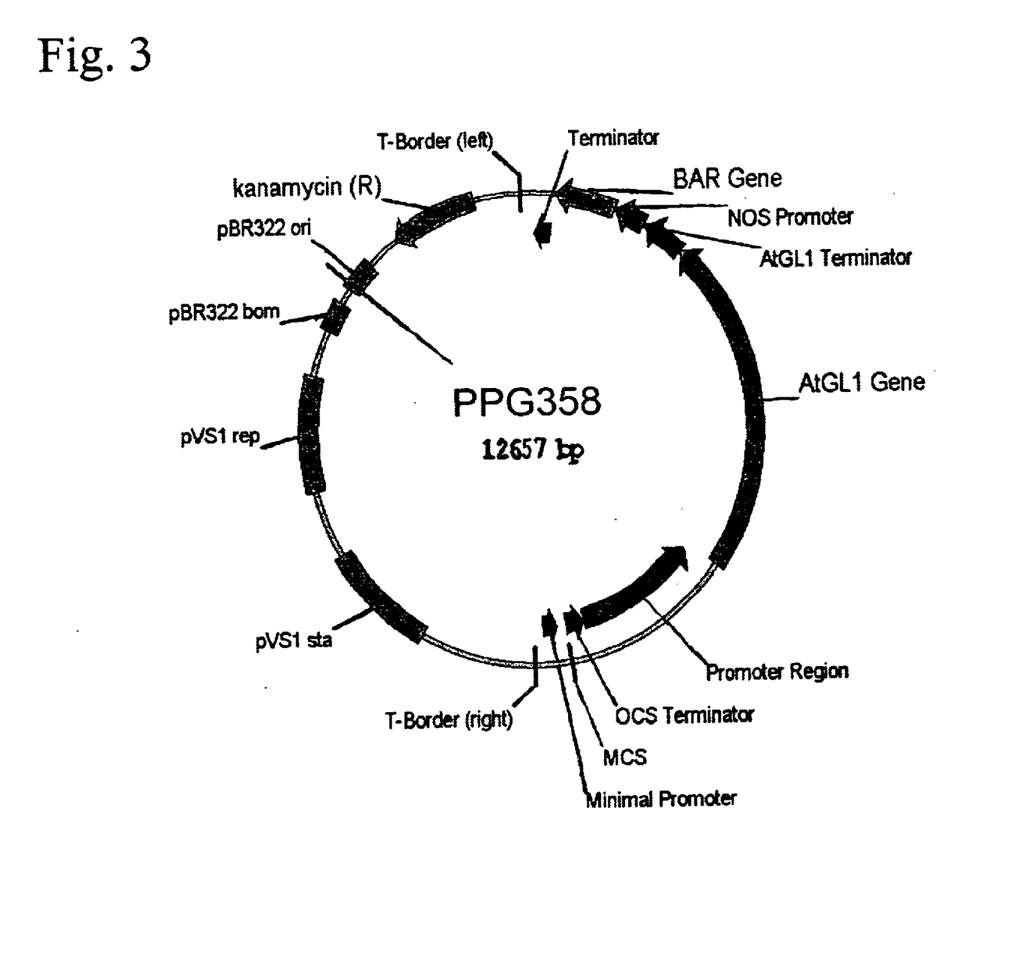
Figure 4:
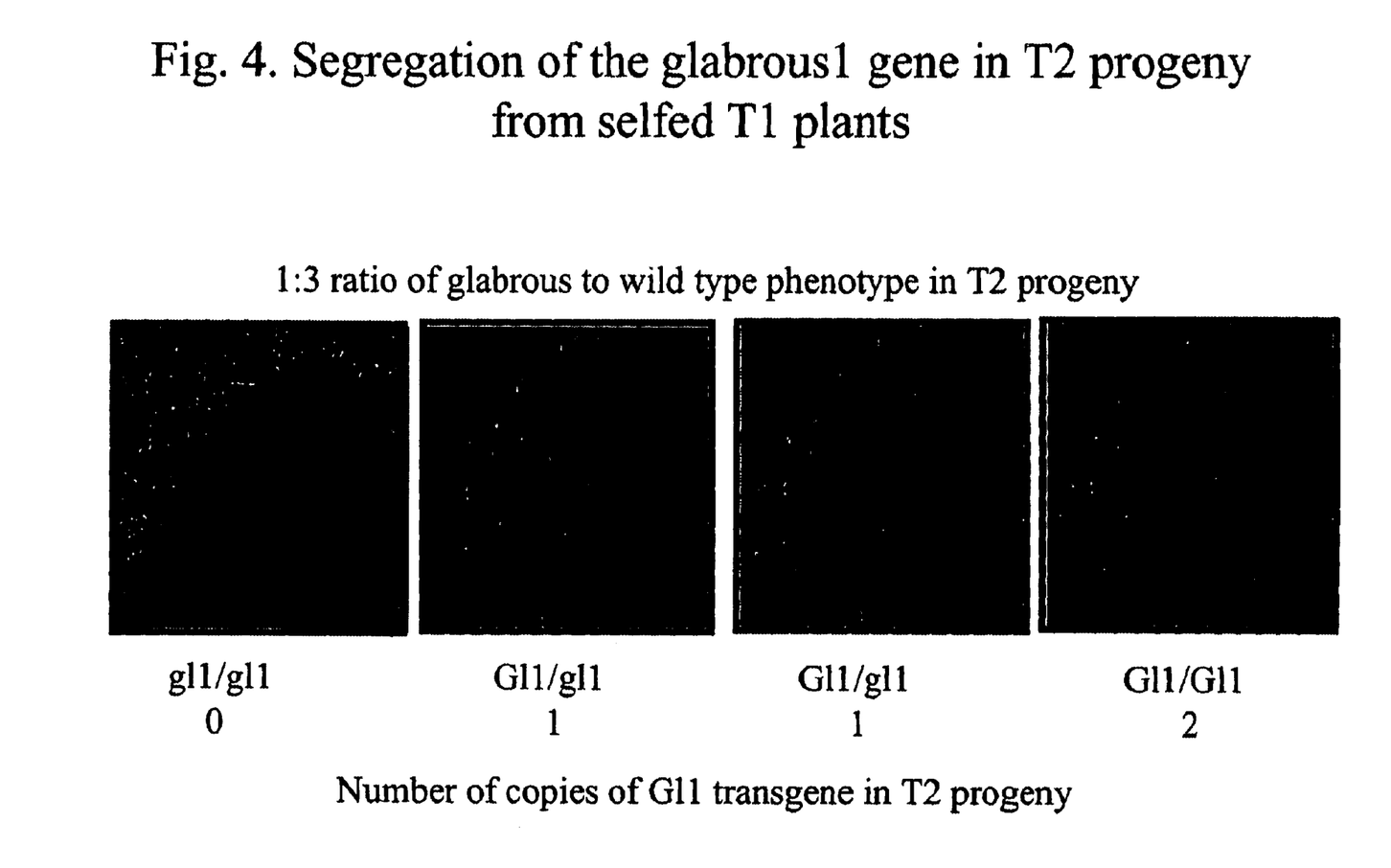
FIG. 4 is a set of photographs further illustrating the predicted outcomes of various crossings of the successfully transformed T1 plants containing one copy of the heterologous gene, expressed in terms of the number of copies of heterologous genes present in the progeny of the crossed T1 plants (T2 plants). When T1 plants with a single transgene are self-crossed, it is expected that ¼ of the progeny plants will have zero copies of the heterologous genes (i.e., the plant is homozygous for the gl1 mutation, labeled as gl1/gl1); these plants will lack trichomes and thus will be visually identifiable. ¼ of the progeny plants will have 2 copies of the heterologous gene (homozygous; labeled as Gl1/Gl1), and ½ of the progeny will have one copy of the heterologous gene (hemizygous; labeled as Gll/gl1); these plants will exhibit trichomes.
Figure 5:
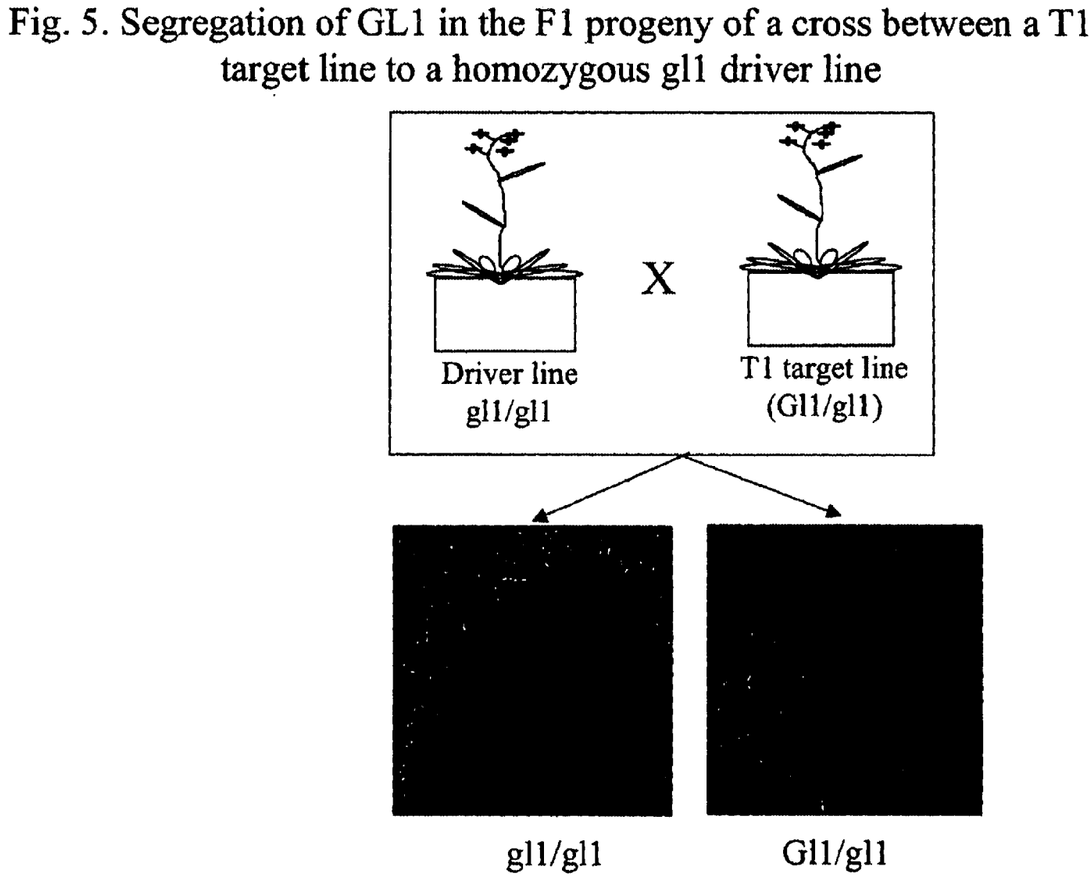
FIG. 5 illustrates that when T1 plants comprising a target DNA construct (with a heterologous gene in addition to the wild type Gl1 gene) are crossed with a driver line (which comprises a DNA construct lacking the GL1 gene and the heterologous gene) in a homozygous gl1 background plant, the result (F1 progeny) is ½ of the progeny plants having zero copies of the heterologous gene (left photograph, lacking trichomes), and ½ of the progeny plants having 1 copy of the heterologous gene (right photograph, trichomes present).
Figure 6:
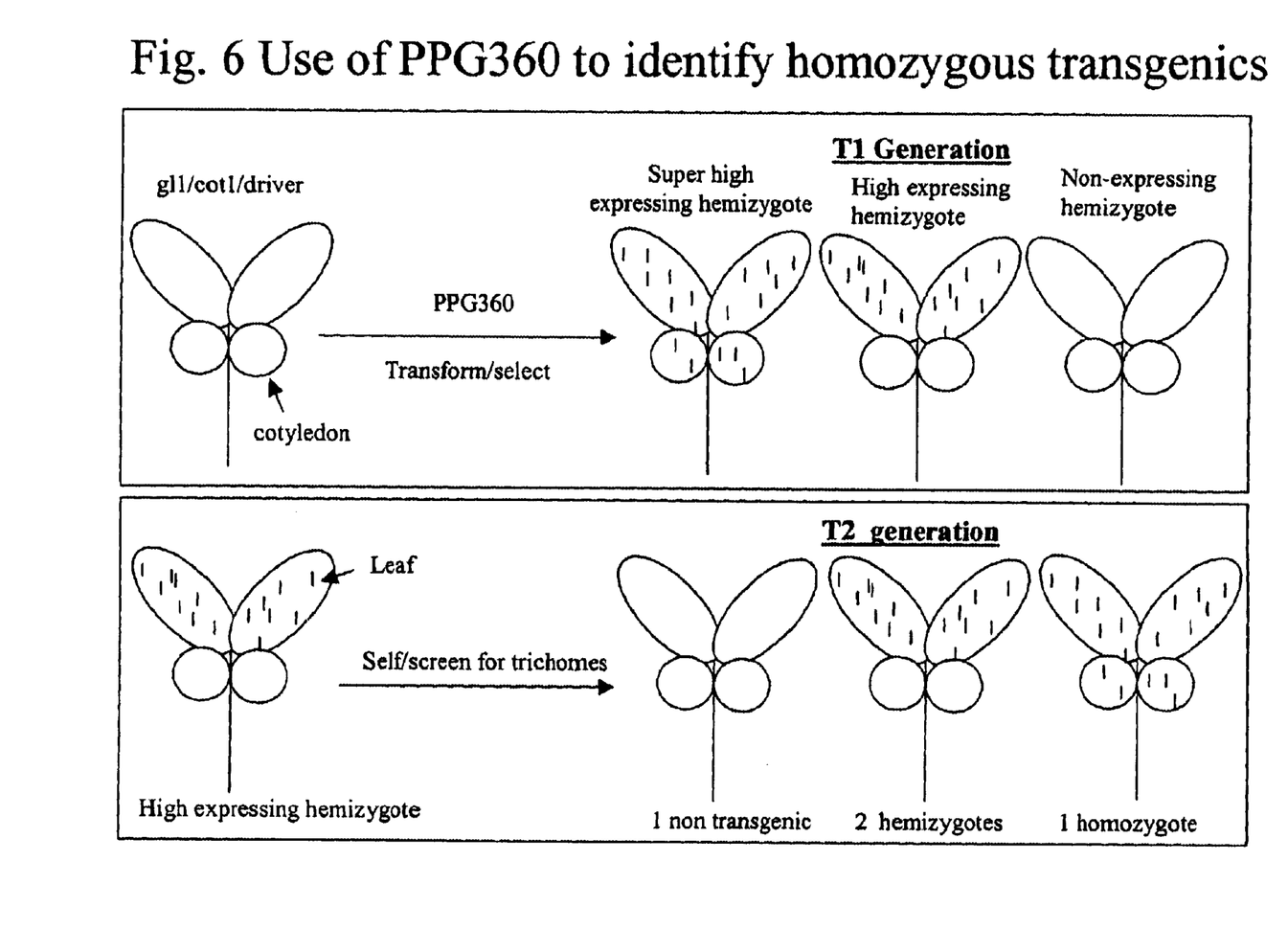
Figure 7:
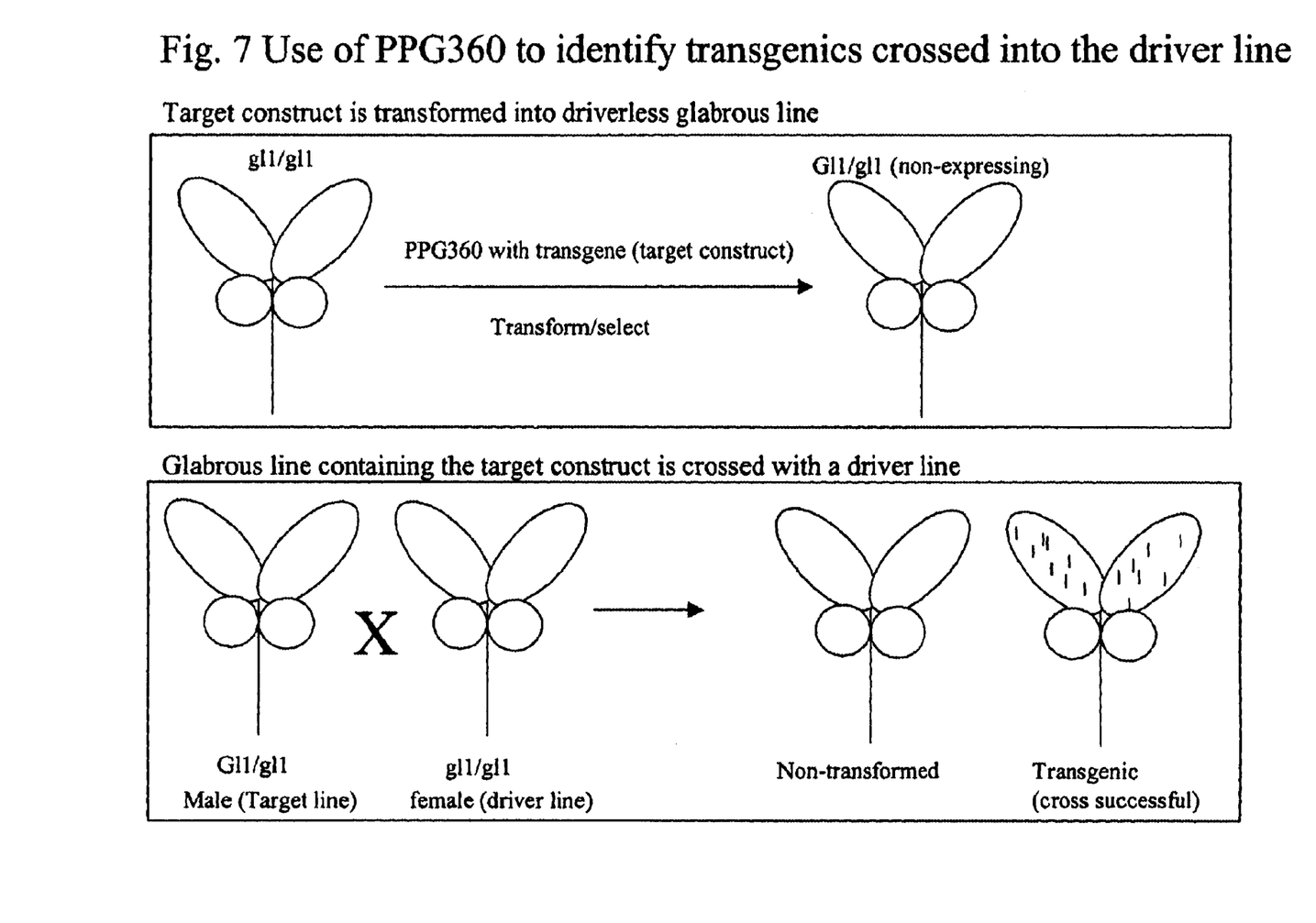

In a preferred embodiment of this invention, using the binary vector PPG360 (see description of FIG. 3) target genes are cloned downstream from a minimal synthetic promoter that is activated when crossed or transformed into a line containing a transcription factor that binds to the promoter. The transactivation strategy results in minimal expression of the target gene in the absence of the transcription factor and very high expression in its presence. By cloning Gl1 behind the minimal synthetic promoter and screening for cotyledon trichomes, the practitioner can identify lines where the expression of Gl1 is high, thereby simultaneously confirming that the transactivation strategy is working and revealing the identity of the homozygotes.

The identification of homozygotes is further aided by the fact that strong expression and homozygosity of the marker is linked to strong expression and homozygosity of the target transgene.

In yet another use of the present invention, the practitioner may use the methods set forth herein to distinguish progeny from successful crosses from progeny of self-crosses. Arabidopsis plants are self-fertile. When crossing two plants, the male parts of the flower are surgically removed and the pollen from a second plant is placed onto the stigma of the emasculated flower. Occasionally self fertilization occurs on plants that have been emasculated. The present invention allows the practitioner to identify the progeny of a successful cross. By using gl1 mutants (i.e., a gl1 background) as the female parent, and pollen from a transgenic plant hemizygous or homozygous for GL1, all successful crosses will result in offspring containing trichomes, whereas self-fertilization will result in progeny lacking trichomes.

The following Examples are provided to illustrate the present invention, and should not be construed as limiting thereof.

EXAMPLES

1. The 4.5 kb genomic fragment used to complement the glabrous 1 mutation is evaluated. The DNA fragment used contains 1.4 kb of promoter, three exons (687 bp), two introns (871 bp), and 1.5 kb of 3' untranslated sequence. In this invention, gl1 is linked to the target gene by cloning both into the same binary vector, PPG360.

2. A vector containing a 3.6 kb Gl1 construct consisting of the native promoter fused to the glabrous1 cDNA and the native terminator is evaluated.

3. A 2.5 kb Gl1 construct consisting of the cDNA flanked by the native promoter and a synthetic terminator is tested. The binary vector is transformed into plants as described above. Plants are selected by spraying the seedlings with the herbicide BASTA™. Herbicide resistant plants are examined for the presence of trichomes on the first true leaves by visual inspection. In this way, the effectiveness of the trichome marker relative to a selectable marker is evaluated.

4. Transgenics and progeny from successful crosses are identified by the following method:

a. Driver constructs are crossed into glabrous1 mutant background (driver/gl1)

b. Gl1 is expressed from its own promoter c. The Gl1 gene is cloned into PPG360, and transgenes are cloned behind the synthetic promoter d. The Gl1 construct is transformed into driver/gl1 or gl1 line e. Transformants are selected using BASTA™ (all transformants should have trichomes)

f. Driver lines are selfed, then screened for trichomes in the T2 progeny (expect 3:1 ratio of trichomes:glabrous) or g. T1 (lacking driver) are crossed to driver/gl1 lines (female parent), then screened for trichomes in the T2 progeny (expected results: a 1:1 ratio of trichomes:glabrous).

5. Transgenics, homozygotes, high trans-activators, and progeny from successful crosses are identified as followed:

a. Driver constructs are crossed into glabrous 1/cod mutant background (driver/gl1/cot)

b. Gl1 is expressed from a synthetic promoter activated by the driver line.

c. The Gl1 gene is cloned into PPG360; transgenes are cloned behind the synthetic promoter.

d. The Gl1 construct is transformed into the driver/gl1/cot1 or gl1 line e. Transformants are selected using BASTA™ (transformants should have trichomes on cotyledons in the driver line, transformants should lack trichomes in the gl1 line)

f. Driver lines are selfed, then screened for trichomes on cotyledons in the T2 progeny (expected results are: trichomeless plants, trichomes only on leaves, and trichomes on leaves and cotyledons), or g. T1 (lacking driver) is crossed to the driver/gl1 line (female parent), and then screened for trichomes in the T2 progeny, (expected results: 1:1 ratio of trichomes: glabrous).

The foregoing is illustrative of the present invention and is not to be construed as limiting thereof. The invention is defined by the following claims, with equivalents of the claims to be included therein.

That which is claimed is:

1. A method of determining the successful transformation of an Arabidopsis plant with a heterologous polynucleotide, comprising:

transforming an Arabidopsis plant with a DNA construct comprising at least one heterologous polynucleotide operatively associated with a promoter capable of regulating transcription in a plant and a wild-type GL1 encoding polynucleotide expressed from its own promoter, wherein the plant is homozygous for a mutation of the GL1 gene;

collecting seeds from the plant and growing the seeds into progeny plants; and detecting the presence or absence of trichomes on the progeny plants, wherein the presence of trichomes indicate the successful transformation of the progeny plants with the heterologous polynucleotide.

2. The method of claim 1 wherein the heterologous polynucleotide is operatively associated with a minimal promoter.

3. The method of claim 2 wherein the heterologous polynucleotide is operatively associated with a 4X AS gal4 minimal promoter.

4. The method of claim 1 wherein the heterologous polynucleotide is operatively associated with a promoter selected from the group consisting of constitutive, inducible, temporally regulated, developmentally regulated, chemically regulated, tissue-preferred and tissue-specific.

5. The method of claim 1 wherein the plant is homozygous for the gl1-1 mutation.

6. The method of claim 1 wherein the transformation of the plant is carried out by a method selected from the group consisting of direct transfer into protoplasts, microprojectile bombardment, injection into protoplasts or cultured cells, electroporation, and Agrobacterium-mediated transformation.

7. The method of claim 1, wherein the transformation is carried out by Agrobacterium-mediated transformation and the DNA construct is an Agrobacterium binary vector.

8. A method of determining the successful transformation of an Arabidopsis plant with a heterologous polynucleotide, comprising:

transforming an Arabidopsis plant with a DNA construct comprising at least one heterologous polynucleotide operatively associated with a promoter capable of regulating transcription in a plant and a wild-type GL1 encoding polynucleotide expressed from a 35S promoter, wherein the plant is homozygous for a mutation of the GL1 gene;

collecting seeds from the plant and growing the seeds into progeny plants; and detecting the presence or absence of trichomes on the progeny plants, wherein the presence of trichomes indicates the successful transformation of the progeny plants with the heterologous polynucleotide.

9. The method of claim 8 wherein the heterologous polynucleotide is operatively associated with a minimal promoter.

10. The method of claim 9 wherein the heterologous polynucleotide is operatively associated with a 4XUAS gal4 minimal promoter.

11. The method of claim 8 wherein the heterologous polynucleotide is operatively associated with a promoter selected from the group consisting of constitutive, inducible, temporally regulated, developmentally regulated, chemically regulated, tissue-preferred and tissue-specific.

12. The method of claim 8, wherein the plant is homozygous for the gl1-1 mutation.

13. The method of claim 8, wherein the transformation of the plant is carried out by a method selected from the group consisting of direct transfer into protoplasts, microprojectile bombardment, injection into protoplasts or cultured cells, electroporation, and Agrobacterium-mediated transformation.

14. The method of claim 8, wherein the transformation is carried out by Agrobacterium-mediated transformation and the DNA construct is an Agrobacterium binary vector.

15. A method of determining the successful transformation of an Arabidopsis plant with a heterologous polynucleotide, comprising:

transforming an Arabidopsis plan with a DNA construct comprising at least one heterologous polynucleotide operatively associated with a promoter capable of regulating transcription in a plant and a wild-type GL1 encoding polynucleotide expressed from a minimal promoter, wherein the plant is homozygous for a mutation of the GL1 gene;

collecting seeds from the plant and growing the seeds into progeny plants; and detecting the presence or absence of trichomes on the progeny plants, wherein the presence of trichomes indicates he successful transformation of the progeny plants with the heterologous polynucleotide.

16. The method of claim 15 wherein the heterologous polynucleotide is operatively associated with a minimal promoter.

17. The method of claim 16 wherein the heterologous polynucleotide is operatively associated with a 4XUAS gal4 minimal promoter.

18. The method of claim 15 wherein the heterologous polynucleotide is operatively associated with a promoter selected from the group consisting of constitutive, inducible, temporally regulated, developmentally regulated, chemically regulated, tissue-preferred tissue-specific.

19. The method of claim 15, wherein the plant is homozygous for the gl1-1 mutation.

20. The method of claim 15 wherein the transformation of the plant is carried out by a method selected from the group consisting of direct transfer into protoplasts, microprojectile bombardment, injection into protoplasts or cultured cells, electroporation, and Agrobacterium-mediated transformation.

21. The method of claim 15 wherein the transformation is carried out by Agrobacterium-mediated transformation and the DNA construct is an Agrobacterium binary vector.

* * * * *